United States Patent

Khanna et al.

[11] Patent Number: 5,861,403
[45] Date of Patent: Jan. 19, 1999

[54] PURINYLALKYL BENZAMIDE DERIVATIVES

[75] Inventors: Ish Kumar Khanna, Vernon Hills; Richard Mathias Weier, Lake Bluff, both of Ill.

[73] Assignee: G. D. Searle & Co., Skokie, Ill.

[21] Appl. No.: 725,307

[22] Filed: Oct. 2, 1996

Related U.S. Application Data

[60] Provisional application No. 60/005,118 Oct. 5, 1995.
[51] Int. Cl.$^6$ .................. A61K 31/52; C07D 473/40; C07D 473/00; C07D 473/30
[52] U.S. Cl. .................. 514/261; 514/262; 514/263; 544/264; 544/265; 544/271; 544/276; 544/277
[58] Field of Search .................. 544/271, 264, 544/265, 276, 277; 514/261, 262, 263

[56] References Cited

PUBLICATIONS

Strickland, Bioworld Today, p. 1.
Guinot, J. Lipid Mediators Cell Signalling 10, 141–146, 1994.
Tang, Drug Devel. Res. 29, 216, 1993.
Fink, Abstract of J. Antimicrobial Chemotherapy 41/Suppl. A, 81–94, 1988.

*Primary Examiner*—Mark L. Berch
*Attorney, Agent, or Firm*—Fitzpatrick, Cella, Harper & Scinto

[57] ABSTRACT

The present invention relates to compounds of the formula

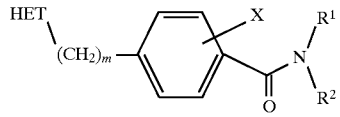

wherein HET is

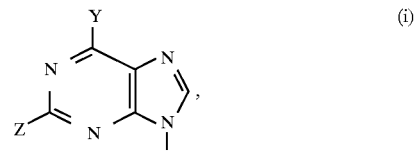

(i)

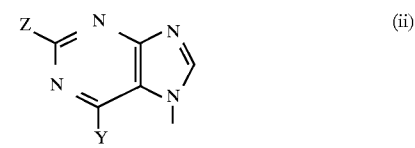

(ii)

and

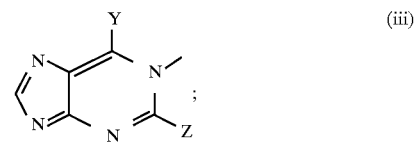

(iii)

m is an integer from 1 to 4;

$R^1$ and $R^2$ are independently selected from the group consisting of linear or branched alkyl of 1 to 6 carbon atoms; and cycloalkyl or cycloalkylalkyl having 3 to 7 ring carbon atoms, the ring carbon atoms optionally substituted with one or more alkyl groups having 1 to about 4 carbon atoms each;

X is a substituent selected from the group consisting of hydrogen, halogen, alkyl, alkoxy, alkoxyalkyl, aminoalkyl, alkylaminoalkyl, dialkylaminoalkyl, alkylthio, and alkylthioalkyl, wherein each of said alkyl moieties has from 1 to about 6 carbon atoms; and Y and Z are independently selected from the group consisting of hydrogen, alkoxy of about 1 to 6 carbon atoms and halogen;

and pharmaceutical compositions containing a therapeutically effective amount of the compounds in combination with a pharmaceutically acceptable carrier and a method for treating diseases mediated by platelet activating factor.

25 Claims, No Drawings

PURINYLALKYL BENZAMIDE DERIVATIVES

This application claims the benefit of U.S. Provisional Application No. 60/005,118, filed Oct. 5, 1995.

FIELD OF THE INVENTION

This invention relates to compounds having platelet activating factor (PAF) antagonist activity which are useful for treating PAF mediated disorders such as asthma, cardiovascular diseases, cerebrovascular diseases, septic shock and the like. The present invention more particularly relates to a class of novel N,N-cycloalkyl/alkyl purinylalkyl-benzamide derivatives which are PAF antagonists.

BACKGROUND OF THE INVENTION

Platelet-activating factor (PAF) has been associated with various biological activities and pathways, thus making it an important mediator responsible for variety of physiological processes, including activation of platelets, smooth muscle contraction, pathogenesis of immune complex deposition, inflammation, and respiratory, cardiovascular and intravascular alterations. These physiological processes are associated with a large group of diseases, such as cardiovascular disorders, asthma, lung edema, septic shock, adult respiratory distress syndrome and inflammatory diseases.

Various classes of compounds are known for inhibiting platelet activation induced by agents such as arachidonic acid, collagen and platelet activating factor. For example, U.S. Pat. No. 4,804,658 discloses a class of imidazopyridine derivatives useful in the treatment of diseases or disorders mediated by platelet-Iizuki, et al. mentions certain classes of imidazoles, which are described as having an inhibitory effect on thromboxane synthetase and as useful for treatment of inflammation, thrombus and asthma. U.S. Pat. Nos. 4,284,641 and 4,416,895 to Thorogood describe certain cycloalkyl/cycloalkenyl imidazoles which inhibit platelet aggregation or reduce the adhesive character of platelets by selective inhibition of thromboxane A2. U.S. Pat. No. 4,537,340 to Thorogood describes a class of 1-arylalkylimidazoles useful for the same purpose. In U.S. Pat. No. 4,243,671 to Harris, et al., the compound 1-(3-phenyl-2-propenyl)1H-imidazole is described as effective in inhibiting thromboxane synthetase, arachidonic acid-induced platelet aggregation and bronchoconstriction.

Compounds are known for use in treating platelet dysfunction or platelet hyperactivity induced specifically by platelet activating factor (PAF). For example, a certain class of glycerol derivatives useful as PAF antagonists is described in EP No. 142,333. A class of indene derivatives is described in EP No. 142,801 as PAF inhibitors. Compounds containing heterocyclic moieties of various types are also known as PAF antagonists. For example, U.S. Pat. No. 4,579,862 to Manley, et al. describes certain imidazole/pyridinylalkanoic acid derivatives as PAF antagonists. U.S. Pat. No. 4,914,108 to Khanna, et al. describes a class of 5-substituted imidazo[4,5-c]pyridine compounds having PAF antagonist activity. U.S. Pat. No. 5,360,907 to Lentz et al. discloses pyrrolo[3,2B]pyridinylalkylbenzamide derivatives which possess PAF antagonist activity.

SUMMARY OF THE INVENTION

This invention relates to a novel class of compounds represented by the formula I

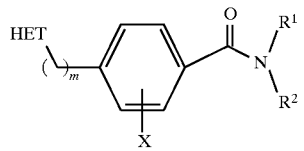

or a pharmaceutically acceptable salt thereof, wherein HET is selected from the group consisting of

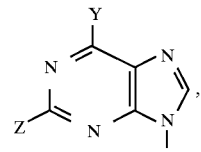

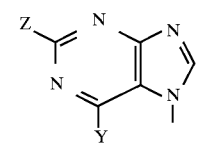

and

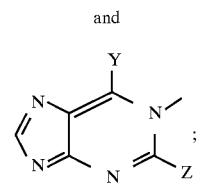

m is an integer from 1 to 4;

$R_1$ and $R_2$ are each independently selected from the group consisting of hydrogen; straight or branched alkyl of 1 to 12 carbon atoms, cycloalkyl having 3 to 8 carbon atoms optionally substituted by one or more alkyl of 1 to 6 carbon atoms, bicycloalkyl having 3 to 8 carbon atoms in each ring, phenyl optionally substituted by one or more groups independently selected from the group consisting of alkyl having 1 to 6 carbon atoms and halogen, straight or branched alkenyl having 3 to 12 carbon atoms, and cycloalkenyl having 3 to 8 carbon atoms;

X is selected from the group consisting of hydrogen, halogen, cyano, hydroxy, amino, straight or branched alkyl of 1 to 6 carbon atoms, alkoxy, alkylthio, alkylamino, aminoalkyl, and hydroxyalkyl, wherein the alkyl moiety has 1 to 6 carbon atoms, alkoxyalkyl, alkylthioalkyl, alkylaminoalkyl, dialkylaminoalkyl, dialkylamino wherein each of the alkyl groups has 1 to 6 carbon atoms; and wherein Y and Z are independently selected from the group consisting of hydrogen, halogen, alkyl, alkoxy and alkylthio, wherein the alkyl moiety has 1 to 6 carbon atoms.

The present invention also provides pharmaceutical compositions comprised of a therapeutically effective amount of a compound of Formula I in combination with a pharmaceutically acceptable carrier and provides a method for treating diseases mediated by platelet-activating factor.

DETAILED DESCRIPTION OF THE INVENTION

This invention encompasses compounds of the Formula I as previously described.

Within the class of compounds defined by Formula I, there is a subclass of preferred compounds represented by the Formula I wherein $R_1$ and $R_2$ are independently selected from the group consisting of straight or branched chain alkyl of 1 to 6 carbon atoms and cycloalkyl of 3 to 7 carbon atoms.

A more preferred subclass of compounds of the Formula I includes compounds wherein X is hydrogen chloro, bromo, fluoro, methyl or methoxy and wherein $R^1$ and $R^2$ independently are isopropyl, cyclopentyl, cyclohexyl, methylcyclohexyl or dimethylcyclohexyl, and wherein Y and Z are independently hydrogen, chloro, bromo or fluoro. Particularly preferred compounds of Formula I include N-cyclohexyl-N-methyl-4-(1H-purin-1-ylmethyl) benzamide; N-cyclohexyl-N-(1-methylethyl)-4-(1H-purin-1-ylmethyl)benzamide; N-cyclohexyl-N-(1-methylethyl)-2-methoxy-4-(1H-purin-1-ylmethyl)benzamide; N-cyclohexyl-N-methyl-4-(7H-purin-7-ylmethyl) benzamide; 4-[(6-chloro-7H-purin-7-yl)methyl]-N-cyclohexyl-N-methylbenzamide; 4-[(6-chloro-7H-purin-7-yl)methyl]-N-cyclohexyl-N-cyclopentyl-3-methoxybenzamide; N-cyclohexyl-2-methoxy-N-(1-methylethyl)-4-(7H-purin-7-ylmethyl)benzamide; N-cyclohexyl-2-methoxy-N-(1-methylethyl)-4-(9H-purin-9-ylmethyl)benzamide; N-cyclohexyl-N-cyclopentyl-3-methoxy-4-(7H-purin-7-ylmethyl)benzamide; N-cyclohexyl-N-cyclopentyl-3-methoxy-4-(9H-purin-9-ylmethyl)benzamide; 4-[(6-chloro-9H-purin-9-yl)methyl]-N-cyclohexyl-N-cyclopentyl-3-methoxybenzamide; N-cyclohexyl-4-[(2,6-dichloro-9H-purin-9-yl)methyl]-N-methylbenzamide; N-cyclohexyl-4-[(9H-purin-9-yl)methyl]-N-methylbenzamide; and 4-[(6-chloro-9H-purin-9-yl) methyl]-N-cyclohexyl-N-methylbenzamide.

Included within the classes and subclasses of compounds embraced by Formula I are isomeric forms of the described compounds including diastereoisomers, enantiomers and tautomeric forms of the described compounds. Pharmaceutically acceptable salts of such compounds are also included as well as pharmaceutically acceptable salts of such isomers and tautomers.

In the structures herein a bond drawn across a bond in a ring indicates that the bond can be to any available atom of the ring structure.

The term "pharmaceutically acceptable salt," as used herein, refers to conventionally accepted pharmaceutical salts prepared by processes which are well known to those of ordinary skill in the art. [See for example, S. M. Berge, et al., "Pharmaceutical Salts," *J. Pharm. Sci.*, 66:1–19 (1977)].

The term "composition" as used herein means a product which results from the mixing or combining of more than one element or ingredient.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The term "alkyl" as used herein means a hydrocarbon (linear or branched) radical having from one to twelve carbon atoms, and more preferably from one to six carbon atoms. Representative of such radicals are methyl, ethyl, n-propyl, isopropyl, n-butyl, sec-butyl, isobutyl, tert-butyl, 2-ethylhexyl, n-octyl, 2,4-dimethylpentyl and the like. The term "lower alkyl" as used herein means an alkyl radical having 1 to 6 carbon atoms.

The term "halogen" or "halo" as used herein means a fluoro, chloro, bromo or iodo radical.

The term amino denotes a radical of the formula —$NH_2$. The term "alkylamino" as used herein is represented by the radical —$NHR_5$ wherein $R_5$ is an alkyl group as previously described. The term "dialkylamino" as used herein is represented by the radical —$NR_6R_5$ wherein $R_6$ and $R_5$ are the same or different alkyl groups, as defined above. The term "aminoalkyl" as used herein is represented by the formula —$R_9NH_2$ wherein $R_9$ is an alkyl group as defined above. The term "alkylaminoalkyl" is represented by the formula —$R_9NHR_8$ wherein $R_8$ and $R_9$ are the same or different alkyl groups.

The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group, such as monofluoromethyl. Dihaloalkyl and polyhaloalkyl groups may be substituted with two or more of the same halo groups, or may have a combination of different halo groups. A dihaloalkyl group, for example, may have two fluorine atoms, such as difluoromethyl and difluorobutyl groups, or two chloro atoms, such as dichloromethyl group, or one fluoro atom and one chloro atom, such as a fluorochloromethyl group. Examples of a polyhaloalkyl are trifluoromethyl, 1,1-difluoroethyl, 2,2,2,-trifluoroethyl, perfluoroethyl, 2,2,3,3-tetrafluoropropyl and perfluoropropyl groups. The term "difluoroalkyl" embraces alkyl groups having two fluorine atoms substituted on any one or two of the alkyl group carbon atoms.

The term "hydroxyalkyl" embraces linear or branched alkyl groups having one to about ten carbon atoms any one or more of which may be substituted with a hydroxyl group.

The term "alkylsilyloxyalkyl" embraces a silyloxyalkylene group wherein such group is attached to the nucleus of Formula I through its alkylene moiety and which group has three terminal alkyl moieties attached to the silyl portion of such group. Similarly, the term "aryl/alkylsilyloxyalkyl" embraces a silyloxyalkylene group wherein such group is attached to the nucleus of Formula I through its alkylene moiety and which group has three terminal moieties selected from alkyl and aryl, which three moieties are attached to the silyl portion of such group. Similarly, the term "arylsilyloxyalkyl" embraces a silyloxyalkylene group wherein such group is attached to the nucleus of Formula I through its alkylene moiety and which group has three terminal aryl moieties attached to the silyl portion of such group.

The term "alkenyl" embraces linear or branched hydrocarbon radicals having two to about twenty carbon atoms, preferably three to about ten carbon atoms, and containing at least one carbon-carbon double bond, which carbon-carbon double bond may have either cis or trans geometry within the alkenyl moiety, relative to groups substituted on the double-bonded carbons. The term "alkynyl" embraces linear or branched hydrocarbon radicals having two to about twenty carbon atoms, preferably two to about ten carbon atoms, and containing at least one carbon-carbon triple bond.

The term "cycloalkenyl" embraces cyclic radicals having three to about eight ring carbon atoms including one or more double bonds between adjacent ring carbons.

The terms "alkoxy" and "alkoxyalkyl" embrace linear or branched oxy containing radicals each having alkyl portions of one to about ten carbon atoms. An example of an alkoxy is a methoxy group. The term "alkoxyalkyl" further embraces alkyl radicals having two or more alkoxy groups attached to an alkyl radical.

The term "alkylthio" embraces radicals containing a linear or branched alkyl group, of one to about ten carbon atoms attached to a divalent sulfur atom, exemplified by a methylthio group. The terms "sulfinyl" and "sulfonyl", whether used alone or linked to other terms such as "alkyl", denote —SO— and —SO$_2$—, respectively.

The term "aryl" denotes a carbocyclic aromatic ring system composed of one or more aromatic rings. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable.

The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical.

The term "cycloalkyl" embraces mono-carbocyclic saturated radicals having three to about eight ring carbon atoms, preferably three to about six carbon atoms, such as cyclopropyl, cyclobutyl, cyclopentyl and cyclohexyl. The term "cycloalkylalkyl" denotes a cycloalkyl radical attached to an alkyl radical which is attachable to a substitutable position of Formula I. Examples of "cycloalkylalkyl" radicals are cyclopentylmethyl and cyclohexylethyl. The term "alkylcycloalkyl" embraces cycloalkyl radicals substituted by one or more alkyl groups as defined above. Examples of alkylcycloalkyl moieties include methycyclohexyl, dimethylcyclohexyl and the like.

The term "cycloalkylhaloalkyl" denotes a cycloalkyl radical attached to a carbon atom of a haloalkyl group as defined above.

The term "formyl" is represented by a radical of the formula —CHO.

The term "cycloalkylcarbonyl" embraces a cycloalkyl radical attached to a "carbonyl" radical of the formula

The term "arylalkylhaloalkyl," as used herein denotes an aralkyl radical as defined above attached via the alkyl portion of the radical to a carbon atom of a haloalkyl radical as defined above.

The term "haloaryl" embraces an aryl radical as defined above substituted on one or more of the ring carbon atoms by the same or different halo radicals as defined above.

The term "aroyl" as used herein denotes an aryl radical as defined above, attached via a ring atom to a carbonyl radical. Representative aroyl radicals include radicals such benzoyl and napthoyl.

The term "bicycloalkyl" as used herein denotes a fused ring system having two fused rings collectively composed of seven to about twelve carbon atoms.

The term "aryloxyalkyl" denotes an aryl radical as defined above attached via a divalent oxygen atom to an alkyl radical as defined above.

The term "alkylcarbonyl" as used herein, denotes an alkyl group as defined above attached to a carbonyl radical as defined above.

The term "alkylcarbonylalkyl" embraces a carbonyl radical as defined above with the same or different alkyl radicals, as defined above, attached to each of its two free valencies.

The term "alkoxycarbonyl" is represented by a radical of the formula —COOR$_7$ wherein R$_7$ is an alkyl group as defined above.

The term "carboxyl" denotes a radical of the formula —COOH.

The term "carboxyalkyl," as used herein, denotes a radical of the formula —R$_7$COOH wherein R$_7$ is an alkyl group as defined above.

The term "alkylcarbonyloxyalkyl" is represented by a radical of the formula R$_8$COOR$_9$— wherein R$_8$ and R$_9$ are the same or different alkyl groups as defined above.

The term "alkoxycarbonylalkyl" is represented by a radical of the formula R$_{24}$OC(O)R$_{25}$— where R$_{24}$ and R$_{25}$ are the same or different alkyl groups as defined above.

The term "aralkoxycarbonylalkyl," as used herein is represented by a radical of the formula R$_{26}$—R$_{27}$—O—C(O)—R$_{28}$— wherein R$_{26}$ is an aryl group as defined above and R$_{27}$ and R$_{28}$ are the same or different alkyl groups as defined above.

The term "aralkylcarbonyloxyalkyl" denotes a radical of the formula R$_{29}$—R$_{30}$—COO—R$_{31}$— wherein R$_{29}$ is an aryl group as defined above and R$_{30}$ and R$_{31}$ are the same or different alkyl groups as defined above.

The term "mercaptoalkyl" as used herein is denoted by a radical of the formula HS—R$_{32}$— wherein R$_{32}$ is an alkyl group as defined above.

The term "alkylthioalkyl" as used herein denotes a radical of the formula R$_{35}$—S—R$_{36}$— wherein R$_{35}$ and R$_{36}$ are the same or different alkyl radicals as defined above.

Compounds of Formula I or their physiologically-acceptable or pharmaceutically-acceptable salts have PAF-antagonistic activity and are of potential value therapeutically as active components in pharmaceutical compositions. Platelet activating factor (PAF) is the phospholipid "1-0-alkyl-2-acetyl-sn-glycero-3-phosphocholine" (AGEPC) which is known as a potent lipid mediator released by animal and human proinflammatory cells. These cells include primarily basophilic and neutrophilic granulocytes, endothelial cells, fibroblasts, epithelial brain cells, macrophages (from blood and tissue) and thrombocytes which are involved in inflammatory reactions.

In pharmacological trials, PAF may cause bronchoconstriction, a lowering of blood pressure, the triggering of thrombocyte aggregation and a proinflammatory activity. Thus PAF is indicated, directly or indirectly, as a mediator in anaphylaxis, in the pathophysiology of allergic conditions, bronchial asthma and in inflammations in general. Compounds of Formula I are therefore suitable for treating patients affected by diseases in which PAF is implicated, including inflammatory or allergic processes or autoimmune diseases. Examples of indications for a PAF antagonist include inflammatory processes of the tracheobronchial tree (acute and chronic bronchitis, bronchial asthma) or of the kidneys (glomerulonephritis), the joints (rheumatic complaints), anaphylactic conditions, allergies and inflammation in the mucous membrances (rhinitis, conjunctivitis) and the skin (e.g. psoriasis, atopic eczema, cold-induced urticaria) and shock caused by sepsis, endotoxins, trauma or burns.

Other important indications for a PAF antagonist include the following: lesions and inflammation in the gastric and intestinal linings, such as shock ulcers, ulcerative colitis, Crohn's disease, ischemic bowel necrosis, stress ulcers and peptic ulcers in general, but particularly ventricular and duodenal ulcers; obstructive lung diseases such as bronchial hyper-reactivity; inflammatory diseases of the pulmonary passages, such as chronic bronchitis; cardio/circulatory diseases such as polytrauma, anaphylaxis and arteriosclerosis; inflammatory intestinal diseases, EPH gestosis (edema-proteinuria hypertension); diseases of extracorporeal circulation, e.g. heart insufficiency, cardiac infarct, organ damage caused by high blood pressure, ischemic diseases, inflammatory and immunological diseases; immune modulation in the transplanting of foreign tissues, e.g. the rejection of kidney, liver and other transplants; immune modulation in leukemia; propagation of metastasis, e.g. in bronchial neoplasia; diseases of the CNS, such as migraine, multiple sclerosis, endogenic depression and agoraphobia (panic disorder). Compounds of Formula I could also be effective as follows: as cyto- and organoprotective agents, e.g. for neuroprotection; to treat DIC (disseminated intravascular coagulation); to treat side effects of drug therapy, e.g. anaphylactoid circulatory reactions; to treat incidents caused by contrast media and other side effects in tumor therapy; to diminish incompatibilities in blood transfusions; to prevent fulminant liver failure ($CCl_4$ intoxication); to treat amanita phalloides intoxication (mushroom poisoning); to treat symptoms of parasitic diseases (e.g. worms); to treat autoimmune diseases (e.g. Werlhof's disease); to treat autoimmune hemolytic anemia, autoimmunologically induced glomerulonephritis, thyroids Hashimoto, primary myxedema, pernicious anemia, autoimmune atrophic gastritis, Addison's disease, juvenile diabetes, Goodpasture syndrome, idiopathic leucopenia, primary biliary cirrhosis, active or chronically aggressive hepatitis (HBsAg-neg.), ulcerative colitis and systemic lupus erythematodes (SLE), ideopathic thrombocytopenic purpura (ITP); to treat diabetes, juvenile diabetes, diabetic retinopathy, polytraumatic shock, haemorrhagic shock; and to treat PAF-associated interaction with tissue hormones (autocoid hormones), lymphokines and other mediators.

The compounds of the present invention can be administered in such oral dosage forms as tablets, capsules, softgels, pills, powders, granules, elixirs or syrups. The compounds can also be administered intravascularly, intraperitoneally, subcutaneously, intramuscularly or topically using forms known to the pharmaceutical art. Moreover, they can be administered rectally, in such forms as suppositories, enemas or bougies. In general the preferred form of administration is oral.

For the orally administered pharmaceutical compositions and methods of the present invention, the foregoing active ingredients will typically be administered in admixture with suitable pharmaceutical diluents, excipients or carriers (collectively referred to hereinafter as "carrier" materials). Such carrier materials are suitably selected with respect to the intended form of administration and consistent with conventional pharmaceutical practices.

For example, for oral administration in the form of tablets or capsules, a therapeutically effective amount of one or more compounds of the present invention can be combined with any oral pharmaceutically acceptable inert carrier such as lactose, starch, sucrose, cellulose, magnesium stearate, calcium sulfate and the like or various combinations thereof. For oral administration in liquid forms, such as in softgels, elixirs, syrups and the like, a therapeutically effective amount of the active drug components can be combined with any oral pharmaceutically acceptable inert carrier such as water, ethanol, polyethylene glycol, vegetable oils, propylene glycol, benzylalcohol and the like or various combinations thereof.

When desired or necessary, suitable binders, lubricants, disintegrating agents, preservatives, and coloring or flavoring agents can also be incorporated into the mixture. Suitable binders include starch, gelatin, natural sugars, corn sweeteners, natural and synthetic gums and waxes and the like, or combinations thereof. Lubricants can include boric acid, sodium benzoate, sodium acetate, sodium chloride and the like, or combinations thereof. Disintegrators include without limitation starch, methylcellulose, agar, bentonite, guar gum and the like, or combinations thereof.

For intravascular, intraperitoneal, subcutaneous or intramuscular administration, one or more compounds of the present invention can be combined with a suitable carrier such as water, saline, aqueous dextrose and the like. For topical administration therapeutically effective amounts of one or more compounds of the present invention can be combined with pharmaceutically acceptable creams, oils, waxes, gels and the like.

Regardless of the route of administration selected, a therapeutically effective amount of the compounds of the present invention are formulated into pharmaceutically acceptable dosage forms by conventional methods known to those skilled in the art. The dosage for preventing or treating PAF mediated conditions with the compounds of the present invention is determined in accordance with a variety of factors, including the type, age, weight, sex and medical condition of patient, the severity of the condition, the route of administration and the particular compound employed in the treatment. A physician or veterinarian of ordinary skill can readily determine and prescribe an effective amount of drug required to prevent or arrest progress of the condition. In so proceeding, the physician or veterinarian could employ relatively low doses at first and subsequently increase the dose until a maximum response is obtained. The daily doses of the compounds of the present invention are ordinarily in the range of about 0.5 mg to about 2000 mg, more preferably in the range of about 350 mg to about 1000 mg.

The compounds of this invention are generally prepared according to reaction schemes I–VII.

SCHEME I

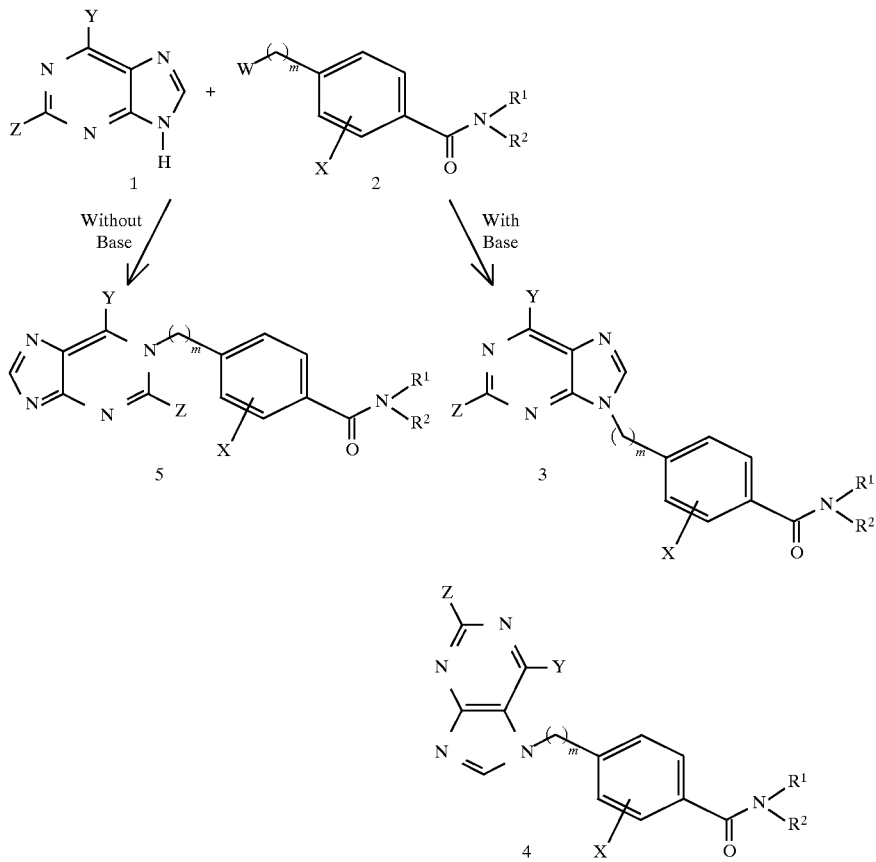

The compounds of Formula I

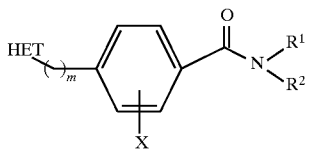

wherein $R^1$, $R^2$, m, and HET are as defined hereinbefore may be synthesized according to the methods depicted in Scheme I above by condensing an optionally substituted purine 1 and a substituted alkylbenzamide derivative 2 either in the presence or absence of base. Purine and a variety of substituted purines are readily obtainable through commercial sources. Among such commercially available purines which are useful in preparing compounds of the present invention are 6-chloropurine, 2,6-dichloropurine, 6-methoxypurine and the like. Additionally, substituted purines may be readily obtained by routine syntheses which are known to those persons of ordinary skill in the art. See, e.g., D. J. Brown, "Fused Pyrimidines, (Part II, Purines)—The Chemistry of Heterocyclic Compounds, A. Weissberger and E. C. Taylor (eds.) Wiley Interscience, New York, 1971. As is known in the art, halo-substituted purines may be used to provide amino-substituted purines, alkoxy-substituted purines, alkylthio-substituted purines and the like using nucleophilic substitution, group interconversion reactions and the like.

A wide variety of substituted alkylbenzamide derivatives 2 may be prepared as described hereinafter with reference to Schemes II through VII.

With reference to Scheme I, compounds of the present invention may be prepared by reacting an optionally substituted purine 1 with a suitably substituted haloalkylbenzamide 2, in an appropriate organic solvent such as acetonitrile or dimethylformamide, preferably in the presence of a crown ether, such as 18-crown-6, at a temperature of from about −30° C. to about 30° C. As shown in Scheme I the reaction is carried out either in the presence or absence of a base depending on the desired product. Carrying out the reaction in the presence of base provides a mixture of compounds of Formula I, wherein the HET moiety is a purin-7-yl moiety or a purin-9-yl moiety (i.e. to provide compounds 3 or 4). Sodium hydride, potassium hydride and the like are suitable bases which may be used. And, where the reaction is carried out in the absence of base, the HET moiety is linked through the 1-position to provide a purin-1-yl compound of Formula I (i.e., compound 5).

SCHEME II

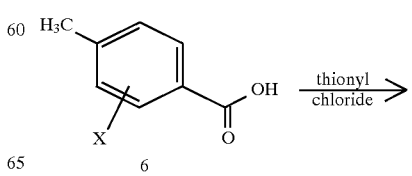

-continued
SCHEME II

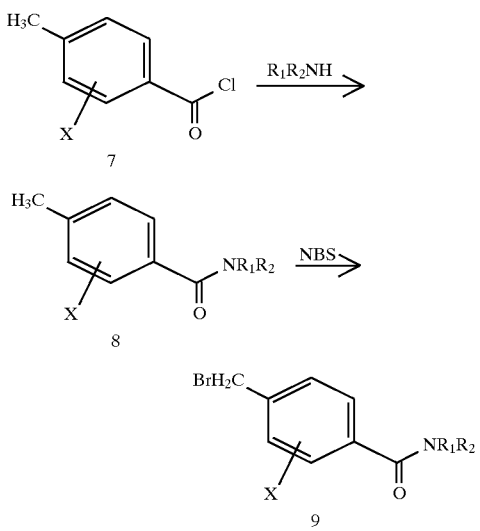

Scheme II shows a method for making haloalkylbenzamides of formula 2 wherein W is Br; X is hydrogen, halogen or alkoxy; and m is 1. In accordance with Scheme II, benzoic acid derivative 6 is converted to its corresponding acid chloride by treatment with a halogenating agent such as thionyl chloride at temperatures of from room temperature to 90° C. Excess thionyl chloride is removed by azeotrope with toluene. The residual acid chloride 7 is dissolved in THF and cooled to −10° C., and a solution of two molar equivalents of an appropriately selected secondary amine [HN($R^1$) ($R^2$), wherein $R^1$ and $R^2$ are defined as above] in THF is added dropwise with stirring. When addition is completed, the reaction is allowed to warm to room temperature and stirred for 1–2 hours to provide compound 8. The reaction is then quenched with 1N HCl diluted with $H_2O$ extracted three times with ethyl acetate, and the combined organic layers are washed with saturated aqueous sodium bicarbonate solution, with water and with saturated aqueous sodium chloride and dried over sodium sulfate. The drying agent is filtered and the filtrate concentrated in vacuo to give a crude product that is chromatographed on silica gel using mixtures of ethyl acetate and hexane as eluents to give the purified amide.

When X is —OMe or —F, in order to properly introduce a leaving group, W, on the methyl group, compound 8 is halogenated with a halogenating agent such as N-bromosuccinimide. N-bromosuccinimide (NBS) may be added to a stirred mixture of the purified amide (1:1 molar ratio) in carbon tetrachloride. The reaction is initiated by irradiation with a sun lamp (150 or 275 W) for 1–3 hours to give a white precipitate which may be filtered and washed with a minimum amount of $CHCl_3$. The filtrate is basified with ammonium hydroxide, washed with water, and the aqueous layer is extracted three times with chloroform. All organic layers are combined, washed three times with saturated aqueous sodium chloride solution and dried over sodium sulfate.

The drying agent is filtered and the filtrate concentrated in vacuo to give a crude product that is chromatographed on silica gel using mixtures of ethyl acetate and hexane to give the purified bromomethyl compound 9.

To provide compound 9 wherein X is a cyano group, amide 8 (X is preferably fluorine or bromine) is reacted with cuprous cyanide or other cyanide reagents in a high boiling solvent such as DMF or collidine prior to treatment with NBS to provide the corresponding cyanide compound 9.

SCHEME III

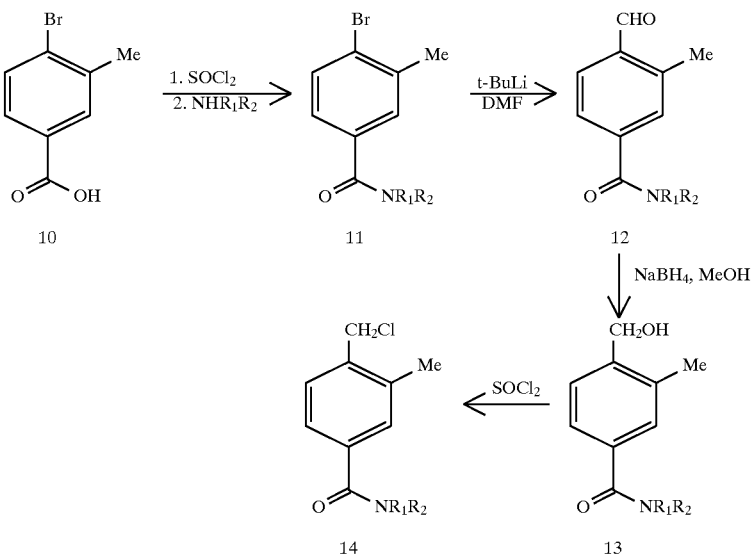

Scheme III depicts an alternative method for preparing haloalkylbenzamides (see e.g., Scheme I, compound 2) wherein W is Cl, m is 1, and X is alkyl. The benzoic acid derivative 14 may be synthesized by converting 4-bromo-3-methyl-benzoic acid 10 to its corresponding benzamide derivative 11 by reaction with thionyl chloride to form the acid chloride of 10 (not shown), followed by reaction of the acid chloride with a predetermined secondary amine (wherein $R^1$ and $R^2$ are defined above) in THF as shown in Scheme II. The bromobenzamide derivative 11 is then treated with an organometallic reagent such as t-butyl lithium and reacted with an electrophile such as dimethylformamide to provide aldehyde 12, which is reduced to alcohol 13 with a reducing agent such as sodium borohydride in the presence of methanol. Alcohol 13 is treated with a halogenating agent such as thionyl chloride to provide the corresponding chloromethyl benzamide 14, which may be utilized in the synthesis depicted in Scheme I to provide compounds of Formula I.

SCHEME IV

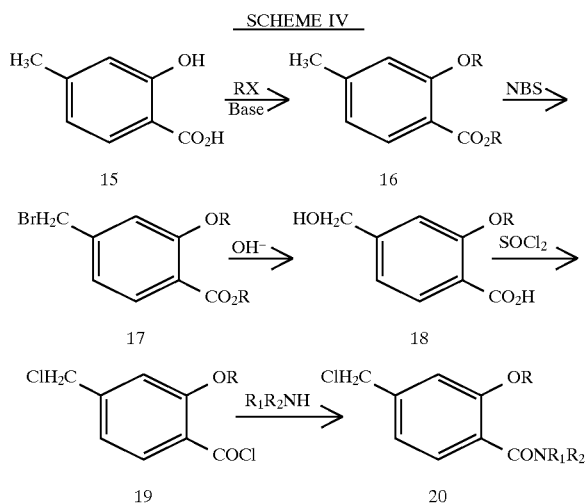

of ester 16 may then be brominated by free radical bromination using N-bromosuccinimide and irradiating the reaction mixture with a sun lamp capable of generating free radicals to provide 4-bromomethyl carboxylic acid ester 17. The ester 17 may be saponified to the corresponding acid with concomitant displacement of the benzylic bromide using a base such as potassium hydroxide in water at temperatures ranging from 80° to ≦100° C. to give the 2-alkoxy-4-hydroxymethyl benzoic acid 18. An organic co-solvent such as dioxane or tetrahydrofuran may be used in order to facilitate dissolution of the organic substrate. Alternatively, compound 34 may be synthesized from bromide 33 in two steps by first, reaction with a metal carboxylate such as sodium acetate or sodium benzoate in an inert solvent such as dimethylformamide, followed by reaction with a suitable base such as potassium hydroxide in an aqueous solvent such as aqueous ethanol or aqueous tetrahydrofuran. Compound 18 is converted to the 4-chloromethyl-2-alkoxybenzoyl chloride 19 by reaction with thionyl chloride at temperatures of from about room temperature to 79° C. The alkoxy-substituted haloalkylbenzamide 20 is produced by reacting compound 19 with a predetermined secondary amine $HNR^1R^2$ in a solvent such as tetrahydrofuran at a temperature of from about 0° C. to about 60° C., and in the presence of a tertiary amine such as triethylamine to act as a hydrochloric acid scavenger.

SCHEME V

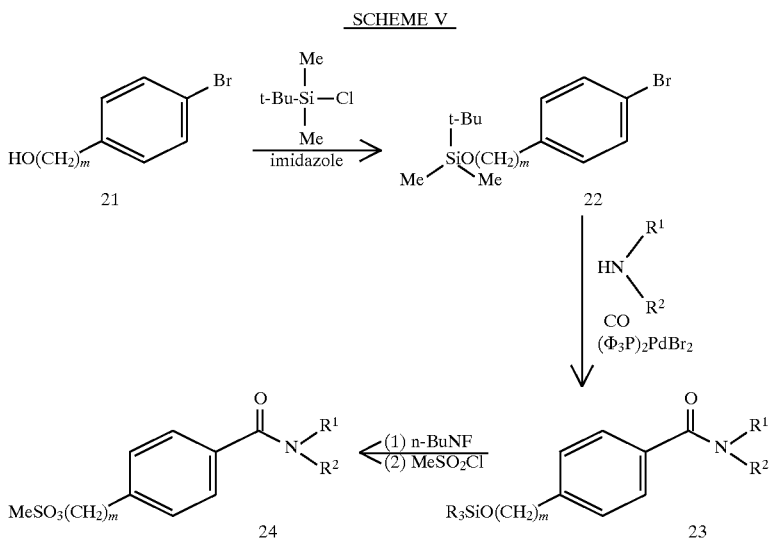

Scheme IV shows an alternative and preferred method of synthesis of haloalkylbenzamides 2 wherein W is Cl, X is alkoxy, and m is 1. 2-Alkoxy-4-chloromethylbenzamides 20 may be synthesized from 2-hydroxy-4-methylbenzoic acid 15. Substituted benzoic acid 15 may be readily converted to its corresponding 2-alkoxy ester 16 using an alkyl halide such as methyl iodide in the presence of a base such as potassium carbonate. The reaction may be conveniently carried out in dimethylformamide at a temperature of from about room temperature to about 60° C. The methyl group Scheme V shows a method for preparing methylsulfonate esters of alkylbenzamides, wherein m is 2 or 3, which esters are useful in preparing compounds of Formula I. With reference to Scheme V, a suitable hydroxyalkyl bromobenzene 21 is silylated to protect the hydroxyl group of compound 21 with a suitable silylating agent such as t-butyldimethylsilyl chloride in the presence of imidazole in a suitable solvent such as dimethylformamide. The silylated aryl bromide 22 is converted to its corresponding carboxamide 23 according to the procedure of Schoenberg et al., J. Org. Chem., 39, 3327(1974), by reaction with carbon monoxide in the presence of bistriphenylphosphinepalladium(II) dibromide as the catalyst and employing the desired secondary amine (HNR$^1$R$^2$) as solvent. The reaction may be carried out at about 100° C. for 8–26 hours in a pressure vessel. The reaction vessel is vented, the reaction mixture triturated with ethyl ether and the washings filtered. The filtrate is washed with 10% aqueous HCl water and brine. After drying over a suitable drying agent, such as magnesium sulfate, and filtering, the filtrate is concentrated and the residue chromatographed on silica gel using mixtures of ethyl acetate and hexane as eluent to give pure product. The silyl ether moiety of compound 23 is removed by reaction with tetra-n-butylammonium fluoride or with an acid such as aqueous acetic acid or dilute hydrochloric acid to provide the corresponding alcohol (not shown), and the alcohol is converted to sulfonate ester 24 by reaction with methanesulfonyl chloride or other suitable alkyl or arylsulfonyl chloride.

accomplished using a presently preferred method which employs methyl substituted 4-cyanobenzoic acid, for example, 4-cyano-3-methyl benzoic acid 25 (see, F. Fichter, G. Shetty, Helv. Chim. Acta, 20, 563 (1937)) as starting material. Compound 25 is converted to the appropriate amide by conversion to the acid chloride with oxalyl chloride, thionyl chloride or other suitable halogenation reagent. Contacting theacid chloride with the appropriate amine provides the desired benzamide 26, which is then treated with a brominating agent such as N-bromosuccinimide to yield the methyl-substituted 4-cyanobenzamide 27. It should be appreciated by the art-skilled that compound 27 is a versatile intermediate which may be used to provide a variety of compounds 2 wherein X is alkoxyalkyl, alkylthioalkyl, alkylaminoalkyl, and the like, by treatment of compound 27 with a suitably reactive derivative of X'. Thus, for example, where the halogen atom ("Hal" of compound 27) is displaced with a

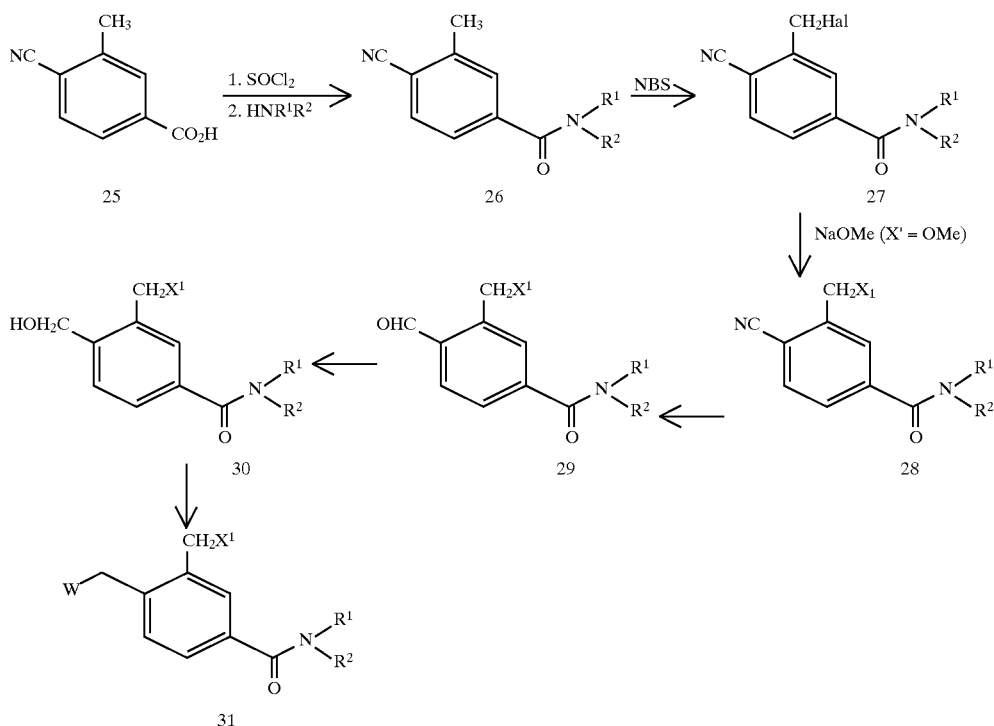

SCHEME VI

Scheme VI shows a general method for the preparation of substituted benzamide compounds of the general formula

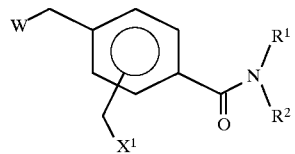

wherein X$^1$ is alkoxy, alkylthio, amino, alkylamino or dialkylamino; W is chloro, bromo, alkanesulfonyloxy, arylsulfonyloxy or p-toluenesulfonyloxy; and R$_1$ and R$_2$ are defined as before. The term "Hal" as used in Scheme VI and the description thereof, means halogen.

Where X$^1$ is alkoxy (i.e. the substituent X of Formula I is alkoxymethyl) introduction of the alkoxy moiety may be metal alkoxide, such as sodium methoxide, the methoxymethyl derivative 28 (X' is OMe) is obtained. Analogously, it will be understood by the art-skilled that displacement of "Hal"with (i) ammonia, (ii) a primary amine or (iii) a secondary amine, respectively, provides the corresponding compound wherein the substituent X is aminomethyl, alkylaminomethyl or dialkylaminomethyl. Alternatively, "Hal" may be displaced with a metal salt of the anion of ammonia, a primary or a secondary amine to produce the same products.

Moreover, it will be appreciated that the halogen (i.e., "Hal") may also be displaced with a metal alkylmercaptide, such as sodium methyl mercaptide, to provide the corresponding alkylthiomethyl-substituted compound.

Conversion of compound 28 to the aldehyde 29 may be effected by controlled reduction with a reducing agent such as diisobutylaluminum hydride, followed by acid hydrolysis. Reduction of aldehyde 29 to the alcohol 30 may be carried out by a second reduction step utilizing a reducing agent such as sodium borohydride or lithium tri-t-butoxyaluminum hydride. Alcohol 30 is converted to a derivative suitable for nucleophilic displacement wherein W is a leaving group such as a halide atom, or aryl sulfonate or alkyl sulfonate moiety by treatment of the alcohol with, for example, thionyl chloride as depicted in Scheme III, p-toluenesulfonyl chloride, methanesulfonyl chloride as shown in Scheme VI, or the like.

Still other haloalkylbenzamides which may be used in the preparation of the compounds of the present 30 invention are disclosed in WO 89/08653 and U.S. Pat. No. 5,019,581, which are incorporated herein by this reference.

A wide variety of secondary amines (sec-amines) of the formula $HNR^1R^2$ are commercially available or may be prepared by known methods which are routine to those having ordinary skill in the art and utilized as intermediates in the preparation of alkylbenzamide derivatives as shown in Schemes II, III, IV, V and VI.

Methods for the preparation of amines, including secondary amines, are well known and described in the literature. See, for example, Emerson, W. S. Org. Reactions 4, 174 (1948); and J. B. Campbell, L. B. Lavaginino in "Catalysis in Organic Syntheses" (Jones W. H., ed.) p. 43, Academic Press, New York, 1980.

A presently preferred method for preparing sec-amines is reductive amination entailing reacting a primary amine and a ketone/aldehyde in a suitable solvent and at a pressure of between about 1 and about 10 atmospheres of hydrogen in the presence of a hydrogenation catalyst such as palladium on carbon, as depicted in the following Scheme. The reaction is preferably carried out at a temperature of from about 25° C. to about 50° C. or more until completion.

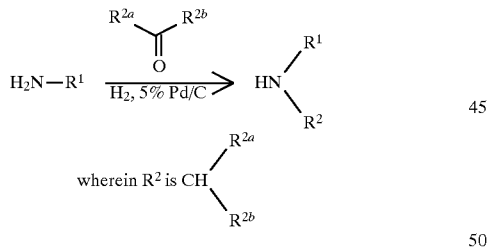

and $R^{2a}$ and $R^{2b}$ are independently hydrogen or alkyl, and $R^{2a}$ and $R^{2b}$ may be optionally linked so that $CHR^{2a}R^{2b}$ is cycloalkyl.

By way of illustration, N-cis,cis-3,5-dimethylcyclohexyl-N-cyclopentylamine may be synthesized as shown in Scheme VII.

SCHEME VII

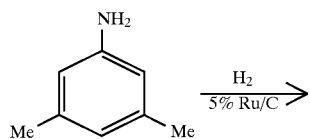

-continued
SCHEME VII

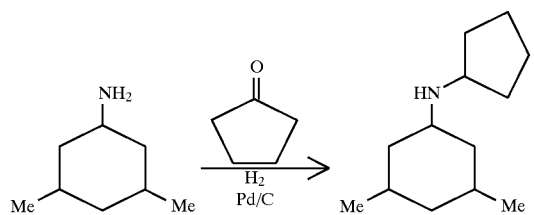

The primary amine, 3,5-dimethylcyclohexylamine, is prepared by catalytic hydrogenation of a 3,5-dimethyl aniline for 7 to 24 hours with a suitable hydrogenation catalyst such as 5% ruthenium on carbon at a pressure of from about 500 to 1500 psi and a temperature of from about 80° to 150° C. N-cis, cis-3,5-Dimethylcyclohexyl -N-cyclopentyl amine is formed by reductive amination of cyclopentanone with 3,5-dimethylcyclohexyl amine. The reductive amination may be carried out by hydrogenation using palladium on carbon as a catalyst at pressures ranging from 15 to 90 psi. The temperature may range from room temperature to 50° C. The reaction time may be from about 7 to 48 hours.

The following examples illustrate the methods used to prepare the compounds of this invention. These Examples are given by way of illustration only and are not meant to be construed as limiting the invention in spirit or scope as many modifications in materials and methods will be apparent from this disclosure to one having ordinary skill in the art. Structural assignments are supported by proton NMR spectroscopy.

EXAMPLE 1

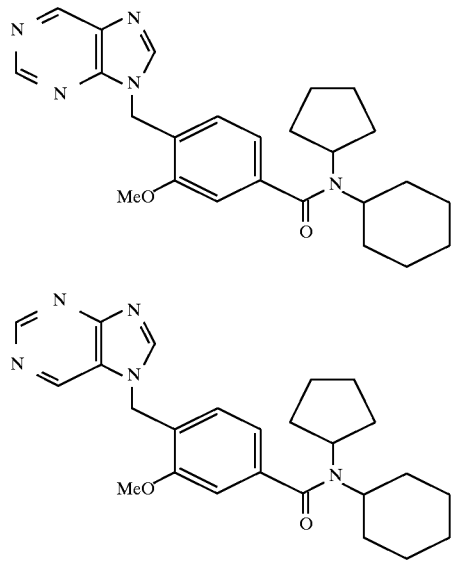

Synthesis of N-cyclohexyl-N-cyclopentyl-3-methoxy-4-(9H-purin-9-ylmethyl)benzamide (1A) and N-cyclohexyl-N-cyclopentyl-3-methoxy-4-(7H-purin-7-ylmethyl) benzamide (1B)

To a stirred solution of purine (310 mg, 2.58 mmol) in acetonitrile (50 mL) were added 18-crown-6 (115 mg, 0.43 mmol) and potassium hydride (104 mg, after ether wash of 35% dispersion in mineral oil, 2.6 mmol) at −20° C. After stirring for 40 min, the reaction was allowed to warm to room temperature and stirred for an additional 1 hr.

4-Bromomethyl-3-methoxy-N-cyclopentyl, N-cyclohexyl benzamide (1.1 g, 2.58 mmol) was added in small amounts over 10 min and the mixture was stirred under argon at 25° C. After 18 hr, the reaction was quenched by adding acetic acid (2 mL) and then neutralized by adding dilute ammonium hydroxide. The solvent was removed under reduced pressure at <45° C. and the crude mixture was chromatographed (silica gel, $CH_2Cl_2$/MeOH 94/6) to give the 1A (410 mg, 37%) and 1B (413 mg, 37%).

1A: m.p. (DSC) 203° C. Anal calcd. for $C_{25}H_{31}N_5O_2.0.2$ $H_2O$: C, 68.69; H, 7.24; N, 16.02. Found: C, 68.88; H, 7.27; N, 15.71.

1B:
mp (DSC) 148°–152° C. Anal calcd. for $C_{25}H_{31}N_5O_2.0.3$ $H_2O$: C, 68.41; H, 7.26; N, 15.95. Found: C, 68.49; H, 7.26; N, 15.93.

EXAMPLE 2

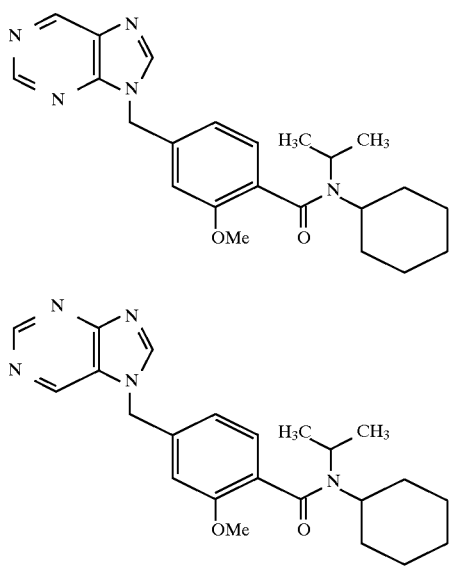

Synthesis of N-cyclohexyl-2-methoxy-N-(1-methylethyl)-4-(9H-purin-9-ylmethyl)benzamide (2A) & N-cyclohexyl-2-methoxy-N-(1-methylethyl)-4-(7H-purin-7-ylmethyl) benzamide (2B)

To a stirred solution of purine (300 mg, 2.52 mmol) in dimethylformamide (25 mL) was added sodium hydride (120 mg, 60% dispersion in mineral oil, 3.02 mmol). After stirring for 2 hr, 4-bromomethyl-2-methoxy-N-isopropyl, N-cyclohexyl benzamide (920 mg, 2.52 mmol) was added in small amounts over 10 min and the mixture was stirred under argon at 25° C. After 20 hr, the reaction was quenched by adding acetic acid (2 mL) and then neutralized by adding dilute ammonium hydroxide. The solvent was removed under reduced pressure at <45° C. and the crude mixture (1.5 g) was chromatographed (silica gel, $CH_2Cl_2$/MeOH/ ammonium hydroxide 90/10/1) to give the 2A (520 mg, 51%) and 2B (290 mg, 28%).

2A: m.p. (DSC) 192° C. Anal calcd. for $C_{23}H_{29}N_5O_2.0.7$ $H_2O$: C, 65.75; H, 7.29; N, 16.67. Found: C, 65.68;. H, 7.10; N, 16.53.

2B: m.p. (DSC) 198° C. Anal calcd. for $C_{23}H_{29}N_5O_2$: C, 67.79; H, 7.17; N, 17.19. Found: C, 67.47; H, 7.22; N, 17.01.

EXAMPLE 3

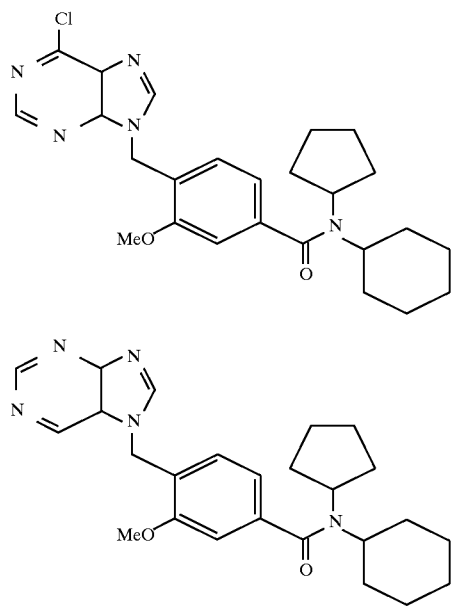

Synthesis of 4-[(6-chloro-9H-purin-9-yl)methyl]-N-cyclohexyl-N-yclopentyl-3-methoxybenzamide (3A) & 4-[(6-chloro-7H-purin-7-yl) methyl]-N-cyclohexyl-N-cyclopentyl-3-methoxybenzamide (3B)

To a stirred solution of 6-chloropurine (400 mg, 2.58 mmol) in acetonitrile (50 mL) at −20° C. was added 18-crown-6 (115 mg, 0.43 mmol) and potassium hydride (104 mg, after ether wash of 35% dispersion in mineral oil, 2.6 mmol). The reaction was allowed to warm to room temperature over 1 hr and stirred for an additional 1 hr. 4-Bromomethyl-3-methoxy-N-cyclopentyl, N-cyclohexyl benzamide (1.1 g, 2.58 mmol) was added in small amounts over 10 min and the mixture was stirred under argon at 25° C. After 18 hr. the reaction was quenched by adding acetic acid (2 mL) and then neutralized by adding dilute ammonium hydroxide. The solvent was removed under reduced pressure at <45° C. and the crude mixture was chromatographed (silica gel, $CH_2Cl_2$/MeOH 94/6) to give pure 3A (480 mg, 39%) and 3B (210 mg, 17%) in addition to a mixture of 3A & 3B (120 mg, 10%).

3A: m.p. (DSC) 194° C. Anal calcd. for $C_{25}H_{30}N_5O_2Cl.0.3$ $H_2O$: C, 63.43; H, 6.52; N, 14.79, Cl 7.49. Found: C, 63.37; H, 6.51; N, 14.35; Cl, 7.98.

3B: m.p. (DSC) 236° C. Anal calcd. for $C_{25}H_{30}N_5O_2Cl.0.7$ $H_2O$: C, 62.48; H, 6.59; N, 14.57. Found: C, 62.11; H, 6.45; N, 14.31.

EXAMPLE 4

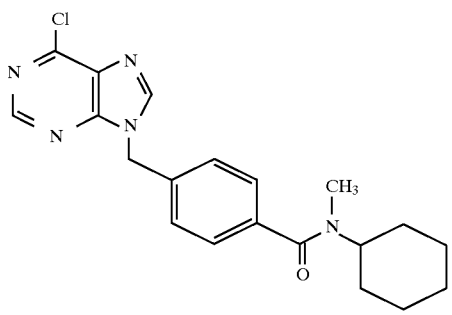

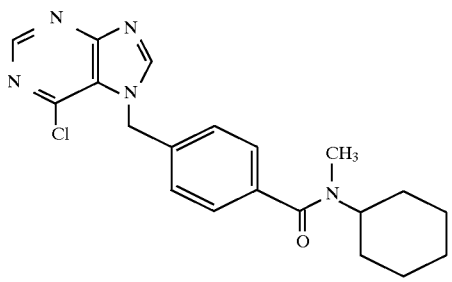

Synthesis of 4-[(6-chloro-9H-purin-9-yl)methyl]-N-cyclohexyl-N-methylbenzamide ( 4A) & 4-[(6-chloro-7H-purin-7-yl)methyl]-N-cyclohexyl-N-methylbenzamide (4B)

To a stirred solution of 6-chloropurine (500 mg, 3.23 mmol) in acetonitrile (50 mL) at −10° C. was added 18-crown-6 (58 mg, 0.22 mmol) and potassium hydride (130 mg after ether wash of 35% dispersion in mineral oil, 3.23 mmol). The reaction was allowed to warm to room temperature and stirred for an additional 30 min. 4-Bromomethyl-N-methyl-N-cyclohexyl benzamide (1.1 g, 3.55 mmol) was added in small amounts over 10 min and the mixture stirred under argon at 25° C. After 18 hr, the reaction was quenched by adding drops of acetic acid and the solvent removed under reduced pressure at <45° C. The residue was dissolved in ethyl acetate and washed with aqueous potassium carbonate, water and brine. The solvent was removed and the crude mixture (1.42 g) chromatographed (silica gel, EtOAc/MeOH 100/2) to give pure 4A (670 mg, 54%) and 4B (210 mg, 17%).

4A: m.p. 164°–165° C. Anal calcd. for $C_{20}H_{22}N_5OCl$: C, 62.58; H, 5.78; N, 18.24; Cl, 9.24. Found: C, 61.96; H, 5.82; N, 18.10; Cl, 9.34.

4B: m.p. 197°–199° C. Anal calcd. for $C_{20}H_{22}N_5OCl$: C, 62.58; H, 5.78; N, 18.24; Cl, 9.24. Found: C, 62.36; H, 5.88; N, 17.91; Cl, 9.11.

EXAMPLE 5

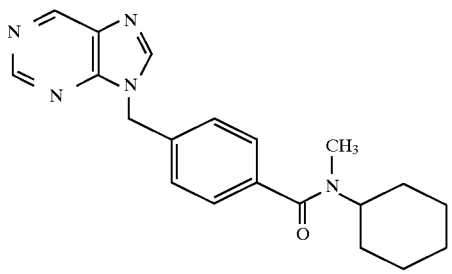

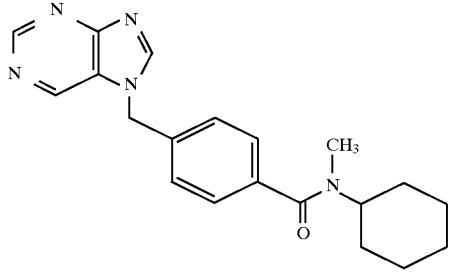

Synthesis of N-cyclohexyl-4-(9H-purin-9-ylmethyl)-N-methylbenzamide (5A) & N-cyclohexyl-4-(7H-purin-7-ylmethyl)-N-methylbenzamide (5B)

To a stirred solution of purine (300 mg, 2.5 mmol) in acetonitrile (30 mL) at −10° C. was added 18-crown-6 (45 mg, 0.17 mmol) and potassium hydride (100 mg after ether wash of 35% dispersion in mineral oil, 2.5 mmol).

The reaction was allowed to warm to room temperature and stirred for an additional 30 min. 4-Bromomethyl-N-methyl-N-cyclohexyl benzamide (477 mg, 1.5 mmol) was added in small amounts over 10 min and the mixture stirred under argon at 25° C. After 18 hr, the reaction was quenched by adding drops of acetic acid and the solvent removed under reduced pressure at <45° C. The residue was dissolved in ethyl acetate and washed with aqueous potassium carbonate, water and brine. The solvent was removed and the crude mixture (570 mg) chromatographed (silica gel, $CH_2Cl_2$/MeOH 100/7) to give pure 5A (167 mg, 32%) and 5B (110 mg, 21%) in addition to mixture of 5A & 5B (140 mg, 27%).

5A: m.p. 140–°-42° C. Anal calcd. for $C_{20}H_{23}N_5O$: C, 68.76; H, 6.59; N, 20.05. Found: C, 68.43; H, 6.76; N, 19.93.

5B: Anal calcd. for $C_{20}H_{23}N_5O$: C, 68.76; H, 6.59; N, 20.05. Found: C, 68.72; H, 6.62; N, 19.84.

EXAMPLE 6

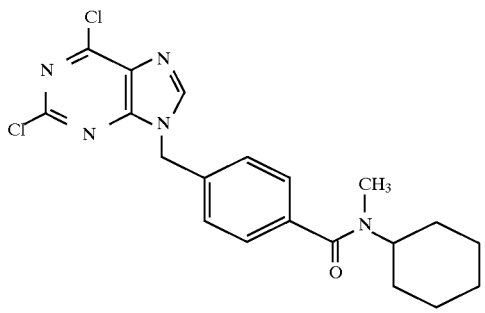

Synthesis of N-cyclohexyl-4-[(2,6-dichloro-9H-purin-9-yl)methyl]-N-methylbenzamide (6A)

To a stirred solution of 2,6-dichloropurine (500 mg, 2.64 minol) in acetonitrile (40 mL)at −10° C. was added 18-crown-6 (48 mg, 0.18 mmol) and potassium hydride (106 mg after ether wash of 35% dispersion in mineral oil, 2.64 mmol). The reaction was allowed to warm to room temperature and stirred for an additional 30 min. 4-Bromomethyl-N-methyl-N-cyclohexyl benzamide (900 mg, 2.90 mmol) was added in small amounts over 10 min and the mixture stirred under argon at 25° C. After 18 hr, the reaction was quenched by adding drops of acetic acid and the solvent removed under reduced pressure at <45° C. The residue was dissolved in ethyl acetate and washed with aqueous potassium carbonate, water and brine. The solvent was removed and the crude mixture (1.28 g) chromatographed (silica gel, CH$_2$Cl$_2$/MeOH 100/7) to give pure 6A (278 mg, 25%). m.p. 134°–136° C. Anal calcd. for C$_{20}$H$_{21}$N$_5$OCl$_2$.0.25 H$_2$O:C, 56.80; H, 5.08; N, 16.56; Cl, 16.80. Found: C, 57.00; H, 5.09; N, 16.20; Cl, 16.59.

EXAMPLE 7

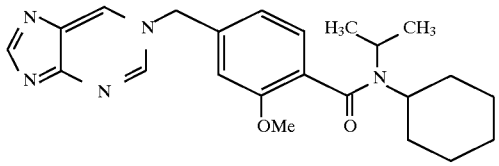

Synthesis of N-cyclohexyl-2-methoxy-N-(1-methylethyl)-4-(1H-purin-1-ylmethyl)benzamide (7)

To a stirred solution of purine (200 mg, 1.6 mmol) in N,N-dimethylformamide (25 mL) was added 4-bromomethyl-3-methoxy-N-isopropyl, N-cyclohexyl benzamide (606 mg, 1.6 mmol). After stirring at room temperature for 26 hr, the solvent was removed under reduced pressure at <45° C. and the residue (1.2 g) chromatographed (silica gel, CH$_2$Cl$_2$/MeOH/NH$_4$OH 90/10/1) to give 7 (580 mg, 89%). Anal calcd. for C$_{23}$H$_{29}$N$_5$O$_2$.0.2 H$_2$O:C, 67.20; H, 7.21; N, 17.03. Found: C, 67.17; H, 7.17; N, 16.91.

EXAMPLE 8

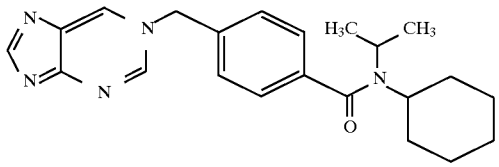

Synthesis of N-cyclohexyl-N-(1-methylethyl)-4-(1H-purin-1-ylmethyl)benzamide (8)

To a stirred solution of purine (310 mg, 2.56 mmol) in N,N-dimethylformamide (20 mL) was added 4 chloromethyl-N-isopropyl, N-cyclohexyl benzamide (750 mg, 1.6 mmol).

After stirring at room temperature for 24 hr, the reaction was immersed in an oil-bath at 70° C. and stirred for 72 hr. The solvent was removed under reduced pressure at <45° C. and the residue (1.2 g) chromatographed (silica gel, CH$_2$Cl$_2$/MeOH/NH$_4$OH 85/15/1.5) to give 8 (370 mg, 38%).

m.p. (DSC) 237° C. Anal calcd. for C$_{22}$H$_{27}$N$_5$O.0.15 H$_2$O: C., 69.50; H, 7.24; N, 18.42. Found: C, 69.43; H, 7.21; N, 18.18.

EXAMPLE 9

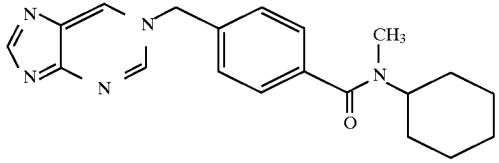

Synthesis of N-cyclohexyl-N-methyl-4-(1H-purin-1-ylmethyl) benzamide (9)

To a stirred solution of purine (300 mg, 2.5 mmol) in N,N-dimethylacetamide (30 mL) was added 4-bromomethyl-N-methyl-N-cyclohexyl benzamide (852 mg, 2.75 mmol). After stirring at 80° C. for 7 hr, the reaction was stirred at room temperature for 16 hr. The solvent was removed under reduced pressure and the residue (510 mg) chromatographed (silica gel, CH$_2$Cl$_2$/MeOH/90/10) to give 9 (310 mg, 35%); m.p. 229°–30° C. Anal calcd. for C$_{20}$H$_{23}$N$_5$O: C, 68.71; H, 6.61; N, 20.05. Found: C, 68.24; H, 6.79; N, 19.77.

BIOLOGICAL EVALUATION

Assay A: Rabbit Platelet Aggregation and Secretion Inhibition Assay

Compounds of the invention were evaluated for their ability to inhibit PAF-induced aggregation of rabbit platelets and serotonin secretion. Rabbit platelet-rich plasma [PRP] was prepared as described in R. Farr et al., Clin. Immunol. Immunopathol. 15:318–330 (1980). All manipulations were done with plastic pipettes and tubes to minimize platelet aggregation. Briefly, 40 ml of arterial blood was collected into 8 ml of acid-citrate-dextrose (ACD)(6.82 grams citric acid, 12.5 grams Na citrate, 10.0 grams dextrose; qs to 500 ml with deionized H$_2$0), gently mixed, and centrifuged at 700 Xg for 20 minutes at room temperature. Approximately 20–25 ml of platelet rich plasma was removed and incubated with 25–30 μCi [$^3$H] serotonin (spec. act.=1 mCi/ml) ([$^3$H]-hydroxytryptamine binoxalate, New England Nuclear, Catalog #NET-398) at 37° C. for 20 minutes with occassional stirring. The lymphocytes were separated from the platelet rich plasma by layering the platelet rich plasma (9 ml) onto 2 ml of lymphocyte separation medium (Histopaque-1077, Sigma Chemical Co., Cat. #1077-1) and centrifuging at 750 Xg for 25 minutes to pellet the lymphocytes. The platelets formed a band at the interface of the plasma and Histopaque and was collected by careful pipetting. The platelets were resuspended in 9 ml of modified Tyrodes medium (8.0 g/l NaCl, 0.195 g/l KCl, 1.02 g/l NaHCO$_3$, 0.213 g/l MgCl$_2$.6H$_2$O, 1.0 g/l α-D(+)glucose, 5.0 g/l gelatin, pH 6.5) supplemented with 0.1 mM EGTA and again layered onto 2 ml of Histopaque and centrifuged at 750 Xg for 25 minutes. The platelets were recovered from the interface and suspended in 9 ml modified Tyrodes without EGTA and centrifuged at 1100 Xg for 15 minutes to pellet the platelets. The pelleted platelets were resuspended in 1–2 ml of modified Tyrodes medium (minus EGTA), counted in a hemacytometer, further diluted in Tyrodes medium (minus EGTA) to a concentration of 1.25×10$^9$/ml and incubated at 37° C. in a humidified atmosphere (5% CO$_2$) until used. Platelet activating factor (PAF) (Sigma Chemical Co., Cat. # P9525) was diluted in 0.9% NaCl, 0.25% bovine serum albumin to a concentration of 2×10$^{-9}$M (final concentration in assay is 2×10$^{-10}$M). 600 μl of serotonin-loaded platelets were added to silicon treated cuvettes with teflon stir bars, and placed in the 37° heating block of the platelet aggregometer [Bio/Data Corporation, Platelet Aggregation Profiler, Model PAP-4]. A predetermined amount of test compound diluted in 6 μl DMSO was added to the cuvette and incubated for 1 minute. 100 μl of platelets were removed as a baseline control for the serotonin secretion assay, and aggregation monitored for 10–15 seconds at 37° with stirring to establish a baseline; platelet aggregation was initiated with the addition of 50 μl PAF. Aggregation was monitored for 3 minutes after addition of PAF. Peak aggregation was considered the peak of the first aggregation wave, usually 45–60 seconds after PAF addition. At 60 seconds after addition of PAF a 100 μl aliquot of platelets was removed for measurement in the serotonin secretion assay. Inhibition of aggregation was determined by the following: 1×[(% aggregation in the presence of compound)÷(% maximal aggregation)]. A log/logit transformation was used to determine half maximal inhibitory concentration of a test compound [$IC_{50}$]. Results are shown in Table I.

Assay B: Human Platelet Receptor Binding

Compounds of the invention were evaluated for their ability to inhibit specific binding of [$^3$H]PAF to human platelet membrane preparation. Human packed platelets were obtained from Lifesource, Inc. (Glenview, Ill.) and washed 3 times with 10 mM Trizma pH 7.0, 2 mM EDTA (dipotassium salt), 150 mM KCl and then once with 10 mM Trizma 7.4, 20 mM $CaCl_2$. The platelets were broken by freezing in a dry ice-ethanol bath, followed by thawing in 24° C. water baths. The preparation was centrifuged (40,000 x g, 20 minutes, 40° C.) and the pellet suspended in 10 mM Trizma 7.4, 20 mM $CaCl_2$, 5 mg/ml human albumin. Protein concentration in the platelet membrane preparation was determined by the Lowry method [O. H. Lowry et al., J. Biol. Chem., 193, 265–275 (1951)]. Aliquots of the membrane preparation were stored at −70° C. Each preparation was characterized for PAF receptor number and dissociation constant (Kd). In binding assays 5 μl of test compound, solubilized in DMSO, was added to polypropylene tubes along with 0.75 nM [$^3$H]PAF and 200 mcl [0.075 nM] of membranes and 95 μl 10 mM Trizma 7.4, 20 mM $CaCl_2$, 5 mg/ml human albumin. Tubes were incubated for 30 minutes at 24° C. The incubation was terminated by adding 4 ml of ice-cold 10 mM Trizma pH 7.4, 20 mM $CaCl_2$ and 20 mg/ml BSA prior to vacuum filtration using Whatman GF/C filters. Filters were prepared and counted in a scintillation counter. All DPM values (disintergrations per minute) were corrected for background and isotope decay. Triplicate determinations for single doses were averaged. The amount of non-specific binding was subtracted from all dose averages, giving an amount of specific binding in all cases. The $IC_{50}$ values for the compounds of the invention were determined by the Allfit program using percent displacement data. (Allfit is a 'basic' computer program for simultaneous curve fitting of a family of signoidal dose-response curves using the four parameter logistic equation.) Results are shown in Table I. In Table 1 "N.D." means not determined; "c-pent" means cyclopentyl; "c-hex" means cyclohexyl; "i-Pr" means isopropyl; "Me" means methyl; and "OMe" means methoxy.

TABLE I

| Example | HET | Y | Z | X | $R_1$ | $R_2$ | Rabbit Platelet Secretion $IC_{60}$ (μM) | Human Platelet Receptor $IC_{60}$ (μM) |
|---|---|---|---|---|---|---|---|---|
| 1A | (pyrimidine-type heterocycle) | H | H | 2-OMe | c-Pent | c-Hex | N.D. | 0.176 |
| 2A | (pyrimidine-type heterocycle) | H | H | 3-OMe | i-Pr | c-Hex | N.D. | 0.136 |
| 3A | (pyrimidine-type heterocycle) | Cl | H | 2-OMe | c-Pent | c-Hex | N.D. | 0.338 |

TABLE I-continued

| Example | HET | Y | Z | X | R₁ | R₂ | Rabbit Platelet Secretion IC₆₀ (μM) | Human Platelet Receptor IC₆₀ (μM) |
|---|---|---|---|---|---|---|---|---|
| 4A | (pteridine, Y,Z substituted) | Cl | H | H | Me | c-Hex | 29 | N.D. |
| 5A | (pteridine, Y,Z substituted) | H | H | H | Me | c-Hex | 12 | N.D. |
| 6A | (pteridine, Y,Z substituted) | Cl | Cl | H | Me | c-Hex | 10 | N.D. |
| 1B | (pteridine isomer, Y,Z substituted) | H | H | 2-OMe | c-Pent | c-Hex | N.D. | 0.555 |
| 2B | (pteridine isomer, Y,Z substituted) | H | H | 3-OMe | i-Pr | c-Hex | N.D. | 44% @ 10 μM |
| 3B | (pteridine isomer, Y,Z substituted) | Cl | H | 2-OMe | c-Pent | c-Hex | N.D. | 0.077 |

TABLE I-continued

| Example | HET | Y | Z | X | R₁ | R₂ | Rabbit Platelet Secretion IC₅₀ (μM) | Human Platelet Receptor IC₅₀ (μM) |
|---|---|---|---|---|---|---|---|---|
| 4B | (structure) | Cl | H | H | Me | c-Hex | 10 | N.D. |
| 5B | (structure) | H | H | H | Me | c-Hex | 57 | N.D. |
| 7 | (structure) | H | H | 3-OMe | i-Pr | c-Hex | N.D. | 40% @ 10 μM |
| 8 | (structure) | H | H | H | i-Pr | c-Hex | N.D. | 19% @ 10 μM |
| 9 | (structure) | H | H | H | Me | c-Hex | 29 | N.D. |

What is claimed is:

1. A compound of the formula or a pharmaceutically acceptable salt thereof wherein HET is selected from the group consisting of

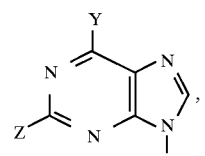 (i)

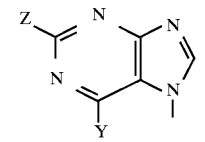 (ii)

and

-continued

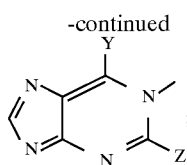
(iii)

m is an integer from 1 to 4;

R¹ and R² are independently selected from the group consisting of linear or branched alkyl of 1 to 6 carbon atoms; and cycloalkyl or cycloalkylalkyl having 3 to 7 ring carbon atoms, the ring carbon atoms optionally substituted with one or more alkyl groups having 1 to about 4 carbon atoms each;

X is a substituent selected from the group consisting of hydrogen, halogen, alkyl, alkoxy, alkoxyalkyl, aminoalkyl, alkylaminoalkyl, dialkylaminoalkyl, alkylthio, and alkylthioalkyl, wherein each of said alkyl moieties has from 1 to about 6 carbon atoms; and Y and Z are independently selected from the group consisting of hydrogen, halogen and alkoxy having from 1 to about 6 carbon atoms.

2. A compound according to claim 1 of the formula wherein HET is selected from the group consisting of:

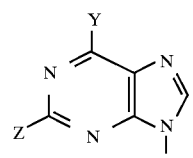
(i)

and

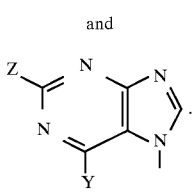
(ii)

3. A compound according to claim 2 wherein m is 1.

4. A compound according to claim 3 wherein at least one of R¹ and R² is cycloalkyl, optionally substituted with one or more alkyl groups.

5. A compound according to claim 4 wherein both R¹ and R² are cycloalkyl, optionally substituted with one or more alkyl groups.

6. A compound according to claim 4 wherein Y and Z are independently hydrogen, chlorine or methoxy.

7. A compound according to claim 6 wherein one of Y and Z is hydrogen, and the other of Y and Z is methoxy.

8. A compound according to claim 3 which selected from the group consisting of:

4-[(6-choloro-7H-purin-7yl)methyl]-N-cyclohexyl-N-cyclopentyl-3- methoxybenzamide;

N-cyclohexyl-N-cyclopentyl-3-methoxy-4-(7H-purin-7-ylmethyl)benzamide;

N-cyclohexyl-2-methoxy-N-(1-methylethyl)-4-(7H-purin-7-ylmethyl)benzamide;

4[(6-choloro-7H-purin-7yl)methyl]-N-cyclohexyl-N-methylbenzamide; and

N-cyclohexyl-N-methyl-4-(7H-purin-7-ylmethyl) benzamide.

9. A compound according to claim 3 which selected from the group consisting of:

N-cyclohexyl-N-cyclopentyl-3-methoxy-4-(9H-purin-9-ylmethyl)benzamide;

4-[(6-chloro-9H-purin-9-yl)methyl]-N-cyclohexyl-N-cyclopentyl-3- methoxybenzamide;

4-[(6-chloro-9H-purin-9-yl)methyl]-N-cyclohexyl-N-methylbenzamide;

N-cyclohexyl-4- (9H-purin-9-ylmethyl)-N-methylbenzamide;

N-cyclohexyl-4[(2,6-dichloro-9H-purin-9yl)-N-methylbenzamide; and

N-cyclohexyl-2-methoxy-N-(1-methylethyl)-4-(9H-purin-9-ylmethyl)benzamide.

10. A compound according to claim 1 wherein HET is

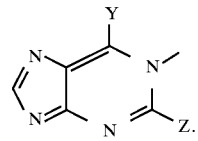

11. A compound according to claim 10 wherein m is 1.

12. A compound according to claim 11 wherein at least one of R¹ and R² is cycloalkyl, optionally substituted with one or more alkyl groups.

13. A compound according to claim 12 wherein both R¹ and R² are cycloalkyl, optionally substituted with one or more alkyl groups.

14. A compound according to claim 12 wherein Y and Z are independently hydrogen, chlorine or methoxy.

15. A compound according to claim 14 wherein one of Y and Z is hydrogen, and the other of Y and Z is methoxy.

16. A compound according to claim 10 which selected from the group consisting of:

N-cyclohexyl-N-(1-methylethyl)-4-(1H-purin-1-ylmethyl)benzamide;

N-cyclohexyl-2-methoxy-N-(1-methylethyl)-4-(1H-purin-1-ylmethyl)benzamide; and

N-cyclohexyl-N-methyl-4-(1H-purin-1-ylmethyl) benzamide.

17. A pharmaceutical composition comprising (A) a compound of the formula:

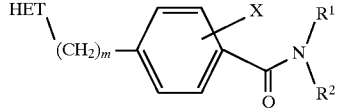

or a pharmaceutically acceptable salt thereof wherein HET is selected from the group consisting of

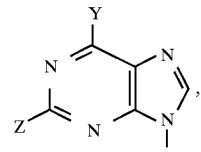
(i)

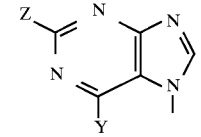
(ii)

and

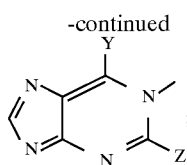

(iii)

m is an integer from 1 to 4;

R¹ and R² are independently selected from the group consisting of linear or branched alkyl of 1 to 6 carbon atoms; and cycloalkyl or cycloalkylalkyl having 3 to 7 ring carbon atoms, the ring carbon atoms optionally substituted with one or more alkyl groups having 1 to about 4 carbon atoms each;

X is a substituent selected from the group consisting of hydrogen, halogen, alkyl, alkoxy, alkoxyalkyl, aminoalkyl, alkylaminoalkyl, dialkylaminoalkyl, alkylthio, and alkylthioalkyl, wherein each of said alkyl moieties has from 1 to about 6 carbon atoms; and Y and Z are independently selected from the group consisting of hydrogen, alkoxy of about 1 to 6 carbon atoms and halogen; and (B) a pharmaceutically acceptable carrier.

18. A pharmaceutical composition according to claim 17 wherein m is 1.

19. A pharmaceutical composition according to claim 17 of the formula wherein HET is selected from the group consisting of:

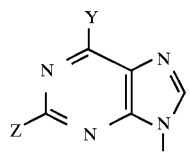

(i)

and

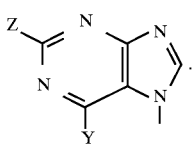

(ii)

20. A pharmaceutical composition according to claim 19 wherein m is 1.

21. A pharmaceutical composition according to claim 20 wherein at least one of R¹ and R² is cycloalkyl, optionally substituted with one or more alkyl groups.

22. A pharmaceutical composition according to claim 21 wherein both R¹ and R² are cycloalkyl, optionally substituted with one or more alkyl groups.

23. A pharmaceutical composition according to claim 21 wherein Y and Z are independently hydrogen, chlorine or methoxy.

24. A pharmaceutical composition according to claim 23 wherein one of Y and Z is hydrogen, and the other of Y and Z is methoxy.

25. A pharmaceutical composition according to claim 17 wherein the compound is selected from the group consisting of:

N-cyclohexyl-N-cyclopentyl-3-methoxy-4-(9H-purin-9-ylmethyl) benzamide;

4-[(6-chloro-9H-purin-9-yl)methyl]-N-cyclohexyl-N-cyclopentyl-3-methoxybenzamide;

4-[(6-chloro-7H-purin-7-yl)methyl]-N-cyclohexyl-N-cyclopentyl-3-methoxybenzamide;

N-cyclohexyl-N-cyclopentyl-3-methoxy-4-(7H-purin-7-ylmethyl) benzamide;

N-cyclohexyl-2-methoxy-N-(1-methylethyl)4-(7H-purin-7-ylmethyl)benzamide;

4-[(6-chloro-7H-purin-7-yl)methyl]-N-cyclohexyl-N-methylbenzamide;

N-cyclohexyl-N-methyl-4-(7H-purin-7-ylmethyl) benzamide;

N-cyclohexyl-2-methoxy-N-(1-methylethyl)-4-(1H-purin-1-ylmethyl)benzamide;

N-cyclohexyl-N-(1-methylethyl)-4-(1H-purin-1-ylmethyl) benzamide;

N-cyclohexyl-N-methyl-4-(1H-purin-1-ylmethyl) benzamide;

4-[(6-chloro-9H-purin-9-yl)methyl]-N-cyclohexyl-N-methylbenzamide;

N-cyclohexyl-4-(9H-purin-9-ylmethyl)-N-methylbenzamide;

N-cyclohexyl-4-(2,6-dichloro-9H-purin-9-yl)methyl]-N-methylbenzamide; and

N-cyclohexyl-2-methoxy-N-(1-methylethyl)-4-(9H-purin-9-ylmethyl)benzamide.

* * * * *